Figure 1:
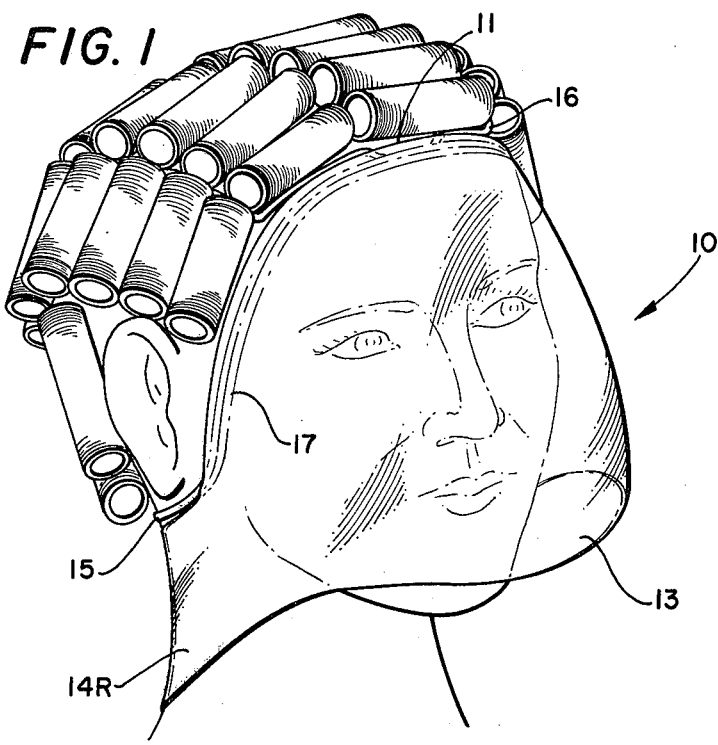

United States Patent [19]

McKee

[11] 4,428,079
[45] Jan. 31, 1984

[54] PROTECTIVE TRANSPARENT FACE AND NECK SHIELD

[76] Inventor: Glenda D. McKee, 1610 Melrose Cir., Garland, Tex. 75042

[21] Appl. No.: 485,883

[22] Filed: Apr. 18, 1983

[51] Int. Cl.³ .......................... A42B 1/18; A61F 9/00
[52] U.S. Cl. ............................................. 2/174; 2/11
[58] Field of Search .................... 2/174, 15, 11, 9, 209

[56] References Cited

U.S. PATENT DOCUMENTS

| | | |
|---|---|---|
| 2,432,767 | 12/1947 | Klein ........................................ 2/174 |
| 3,038,470 | 6/1962 | Campbell ................................ 2/174 |
| 3,241,155 | 3/1966 | Phillips ................................... 2/174 |

Primary Examiner—Doris L. Troutman
Attorney, Agent, or Firm—Warren H. Kintzinger

[57] ABSTRACT

A face and neck protective shield for protection against waving lotion, neutralizer or any other treatment used on the head with the shield generally put on the user's head after the hair is rolled for a permanent prior to application of waving lotion. The shield can be removed during hair rinse and then put back on during application of neutralizer. The shield is cut as one piece of transparent plastic with an enlarged central portion designed to shield substantially the users entire face from the forehead hair line down and two side extensions that wrap around the neck sides and back with overlap at the neck back. Two tie strips are provided on the shield with one strip being held in a folded over strip at the top of the shield extended through the central portion and into the side extensions of the shield to be twist tied at the back of a user's neck each time it is used. The other tie strip is fastened through a relatively short mounting distance at the top of the central portion to extend between curls to be twist tied at the top of the back of the user's head. The shield may be in the form of disposable shields included with permanent wave kits or other hair treatment kits, or more sturdy form as reusable shields for use in beauty salons.

12 Claims, 4 Drawing Figures

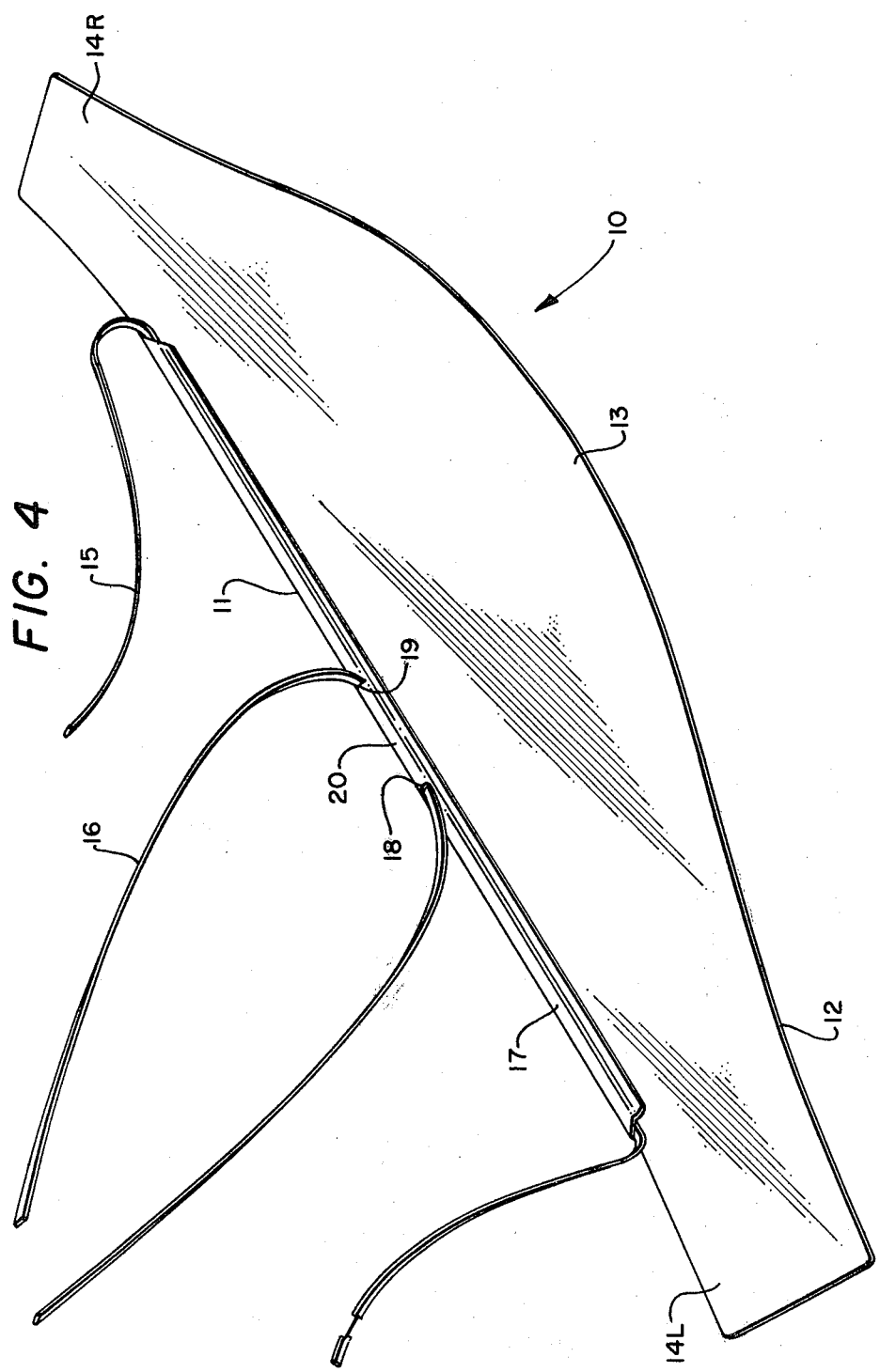

PROTECTIVE TRANSPARENT FACE AND NECK SHIELD

This invention relates in general to face protective shield, and more particularly, to a flexible see through face shield useable during hair permanent wave and beauty treatments.

During hair permanent wave and beauty treatments and additional treatments such as hair dyeing fumes and treatment solution or dye may get in the user's eyes and on the user's face and neck or inhaled by the person receiving the treatment. This can not only be irritating and annoying but also, in some incidents, hazardous. While there have been various face shields provided in the past many of these have not given the protection desired, are awkward to use, not disposable and/or expensive. Further, it is important that there be a minimum of absorbent material in a protective shield to avoid harsh solutions from being absorbed in elastic or padding resting against the skin such as to burn or otherwise irritate the skin once elastic or padding is saturated.

It is, therefore, a principal object of this invention to provide an improved face protective shield primarily of see through plastic and tie down strips without substantially any absorbent material a part of the face shield.

Another object is to provide such a face protective shield in inexpensive disposable form.

Still another object is for such a face protective shield to cover and protect substantially the entire face from the top of the forehead under the hairline down and around neck sides and back.

A further object is to provide such a face and neck protective shield that has tie strips facilitating quick easy mounting of the shield on a person's face and neck when shield protection is needed during a hair beauty treatment.

Another object is to provide such a face shield of flexible transparent plastic with two tie strips that is foldable in the form of disposable shields included with permanent wave kits or other hair treatment kits.

Still another object is to provide such a face shield in more sturdy form as a reuseable shield suitable for use in beauty shops.

Features of the invention useful in accomplishing the above objects include, in a protective see through transparent flexible plastic face and neck shield for protection against waving lotion, neutralizer and other materials used in hair and scalp treatments, a shield structure of generally non absorbent material with one piece of transparent plastic having an enlarged central portion and two side extensions and two tie strips. The shield enlarged central portion shields substantially the user's entire face from the forehead hair line down and the two side extensions wrap around the user's neck sides and back with an overlap at the neck back when properly mounted on a user's head. Two tie strips are provided on the shield with one strip being held in a folded over strip extended along the top of the shield through the central portion and into the side extensions thereof to be twist tied at the back of the neck. The other tie strip is fastened through a relatively short mounting distance at the top of the central portion to be twist tied at the top of the back of the user's head each time the shield is mounted in place for user protection.

A specific embodiment representing what is presently regarded as the best mode of carrying out the invention is illustrated in the accompanying drawings.

Figure 2:
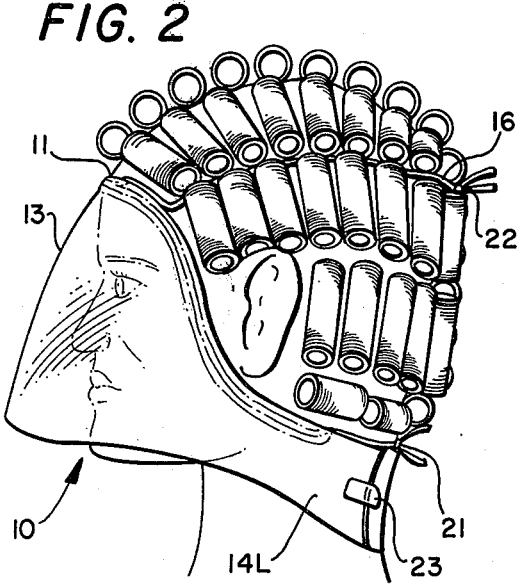
Figure 3:
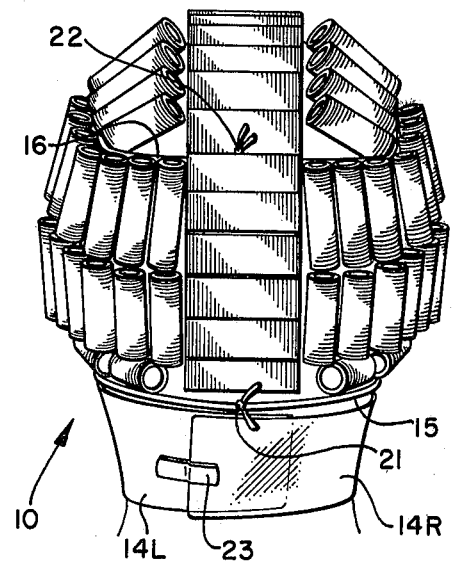

In the drawings:

FIG. 1 represents a perspective view of the new improved face protective see through shield mounted on a user's head;

FIG. 2, a side elevation of the face shield mounted on a user's head showing mounting detail;

FIG. 3, a back elevation of a user's head with additional detail of the tie strip mounting of the shield thereon; and FIG. 4, a perspective view of the face shield with tie strips in the non-mounted state.

Referring to the drawings:

The transparent face shield 10 is shown in FIGS. 1 and 2 to overlap substantially the entire face of the user and while flexible is stiff enough to stand out generally from the face progressively from contact with the face at the top 11 adjacent the user's hairline across the top center and down the sides. The shield 10 is primarily cut as one piece 12 of transparent flexible plastic with an enlarged center portion 13 designed and proportioned to shield substantially the user' entire face from the forehead hair line down. Opposite side extensions 14R and 14L from the enlarged center portion 13 wrap around the neck sides and back with, generally, an overlap at the neck back (refer also to FIGS. 3 and 4).

The see through transparent face shield 10 is also provided with a lower neck tie strip 15 and an upper head tie strip 16. The lower neck tie strip 15 is held in a folded over plastic strip 17 extended through the transverse extent of the center section and on into a portion of each of the opposite side extensions 14R and 14L. The upper head tie strip 16 is fastened through a relatively short mounting distance at the top of the enlarged central portion 13 shown in FIG. 4 to be inserted through openings 18 and 19 in folded over plastic strip 17 to extend through the central portion 20 thereof. The folded over plastic strip 17 can (and is in some instances) also be thermo bonded down to further fix the tie strips 15 and 16 in place. The tie strips 15 and 16 are of the metal wire encased in strip plastic (or paper ribbon) type that lend themselves to being twist tied. When the face shield 10 is being mounted in place on a user's head the lower neck tie strip 15 is twist tied in knot 21 and the upper head tie strip 16 is twist tied in knot 22 at the top of the back of the user's head. The face shield 10 is put on a user's head, for example, after hair is rolled for a permanent wave beauty treatment before application of waving lotion with the tie strip 16 advantageously passed between hair rollers that aid in holding the tie strip 16 in place and thereby the shield 10 in proper sustained mounting on a user. Thus, a plastic face and neck shield 10 is provided with no elastic or padding at mounting edges thereof next to the face that would tend to absorb solution that could become saturated to hold solution on and burn the user's skin and/or seep through once elastic or padding became saturated. It should be noted that the face shield 10 can be removed during rinse and then put back on a user's head before using neutralizer solution on the user's hair. The tie strips 15 and 16 may be fastened to the top of the transparent plastic piece 12 by other than just the folded over plastic strip 17 shown in that they may be bonded or sewn onto the top of the shield or any combination thereof, perhaps even stapled in place. The folded over strip 17 does, however, beneficially present a rounded edge 11 that presses against a user's forehead below the hair line rather than a sharp edge. The face shield 10 in both the relatively light flexible disposable form or in a heavy reuseable form are sufficiently strong to stand away from the face at a slope from the top edge thereof to avoid disturbing cosmetic makeup on the user's face and as an aid to breathing up from below the mask. An additional fastening aid may be provided in the area of overlap at the back of the neck between ends of opposite side extensions 14L and 14R in the form of adhesive tape 23 that in the alternate could be an interlock tape such as that on the market called VELCRO.

Whereas this invention has been described with respect to a preferred embodiment thereof, it should be realized that various changes may be made without departing from the essential contributions to the art made by the teachings hereof.

I claim:

1. A protective transparent face and neck shield comprising: one transparent plastic piece having an enlarged central section proportioned to shield substantially a user's entire face from the forehead hairline down, and two side extensions positioned to wrap around neck sides below the ears and the back of the neck; tie strip means attached to the top of said transparent plastic piece including, a first tie strip attached to the top of said transparent plastic piece through a distance transversely substantially the same as the transverse extent of said enlarged central section with end extensions long enough to be tied at the back of a user's neck; and a second tie strip attached to the top of said transparent plastic piece through a transverse extent shorter than the fastening extent of said first tie strip with end extensions extended to be tied at the upper back of a user's head.

2. The protective transparent face and neck shield of claim 1, wherein the portion of said one transparent plastic piece in contact with a user's skin when the shield is mounted in place on a user's head and neck are of non-fluid absorbent plastic.

3. The protective transparent face and neck shield of claim 2, wherein a fold over strip extends along the top of the shield and into the side extensions that in the folded over state presents a rounded shield edge that is brought into contact with a user's skin when the shield is mounted in place on a user's head.

4. The protective transparent face and neck shield of claim 3, wherein said first tie strip extends through the transverse length of and is enclosed within said foldover strip.

5. The protective transparent face and neck shield of claim 4, wherein said second tie strip is fastened above said first tie strip through a transverse extent along the top of the shield shorter than the fastening extent of said first tie strip.

6. The protective transparent face and neck shield of claim 5, wherein said second tie strip is inserted through a portion of the transverse length of said fold over strip.

7. The protective transparent face and neck shield of claim 6, wherein said fold over strip is plastic thermobonded in the folded over state encapsulating portions of said first and second tie strips.

8. The protective transparent face and neck shield of claim 7, wherein said first and second tie strips are of the metal wire encased in a ribbon of plastic type that lend themselves to being twist tied.

9. The protective transparent face and neck shield of claim 5, wherein said first and second tie strips are of the metal wire encased in a ribbon of plastic type that lend themselves to being twist tied.

10. The protective transparent face and neck shield of claim 2, wherein said first and second tie strips are of the metal wire encased in a ribbon of plastic type that lend themselves to being twist tied.

11. The protective transparent face and neck shield of claim 3, wherein said two side extensions are sufficiently long to overlap at the back of the user's neck.

12. The protective transparent face and neck shield of claim 11, wherein side extension interconnect fastening tape is provided in the area of side extension overlap at the back of a user's neck.

* * * * *